(12) United States Patent
Saidman et al.

(10) Patent No.: US 6,905,081 B2
(45) Date of Patent: Jun. 14, 2005

(54) APPARATUS AND METHODS FOR APPLYING ADHESIVE FILAMENTS ONTO ONE OR MORE MOVING NARROW SUBSTRATES

(75) Inventors: Laurence B. Saidman, Duluth, GA (US); Raza Hayder, Duluth, GA (US); Mehmet Sinangil, Duluth, GA (US)

(73) Assignee: Nordson Corporation, Westlake, OH (US)

( * ) Notice: Subject to any disclaimer, the term of this patent is extended or adjusted under 35 U.S.C. 154(b) by 217 days.

(21) Appl. No.: 10/283,889

(22) Filed: Oct. 30, 2002

(65) Prior Publication Data

US 2004/0112983 A1 Jun. 17, 2004

(51) Int. Cl.[7] .............................. B05B 1/28; B05B 7/10
(52) U.S. Cl. ..................... 239/290; 239/291; 239/292; 239/295; 239/296; 239/298; 239/406
(58) Field of Search ................................ 239/406, 290, 239/291, 292, 295, 296, 298, 451, 456, 225.1; 427/286, 208.2, 208.4; 156/161, 229

(56) References Cited

U.S. PATENT DOCUMENTS

| | | | |
|---|---|---|---|
| 4,785,996 A | 11/1988 | Ziecker et al. | 239/298 |
| 4,844,003 A | 7/1989 | Slautterback et al. | 118/323 |
| 4,960,619 A | 10/1990 | Slautterback et al. | 427/265 |
| 5,507,909 A | 4/1996 | Rollins et al. | 156/425 |
| 6,077,375 A | 6/2000 | Kwok | 156/161 |
| 6,197,406 B1 | 3/2001 | Kwok | 428/195 |
| 6,200,635 B1 | 3/2001 | Kwok | 427/286 |
| 6,361,634 B1 | 3/2002 | White et al. | 156/161 |
| 6,461,430 B1 | 10/2002 | Kwok | 118/325 |

*Primary Examiner*—Davis Hwu
(74) *Attorney, Agent, or Firm*—Wood, Herron & Evans, L.L.P.

(57) ABSTRACT

Apparatus and methods for applying adhesive to one or more narrow substrates, such as elastic strands, that are in motion. The apparatus includes a coating applicator and an air moving device mounted adjacent to the coating applicator. The coating applicator is capable of applying adhesive in the form of an adhesive filament in a pattern onto each narrow substrate. The air moving device includes one or more air discharge passages capable of directing a flow of air toward the narrow substrate. The flow of air transfers momentum to airborne sections of the adhesive filament for promoting coating uniformity on the narrow substrate.

12 Claims, 4 Drawing Sheets

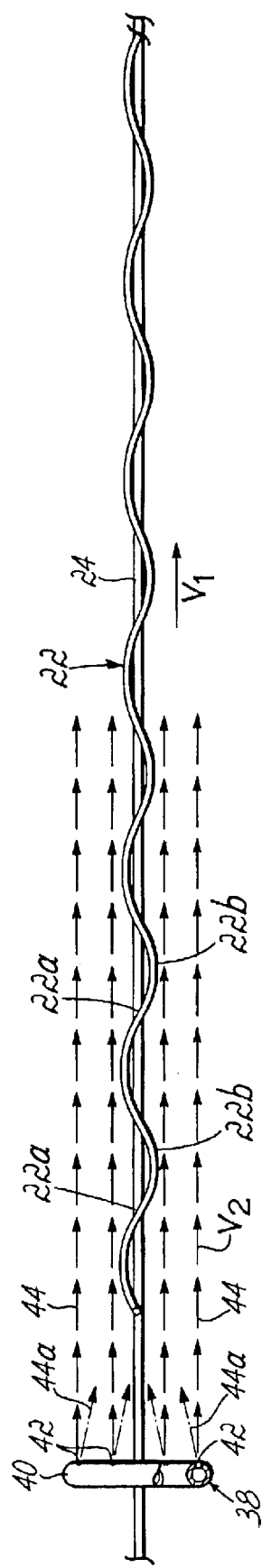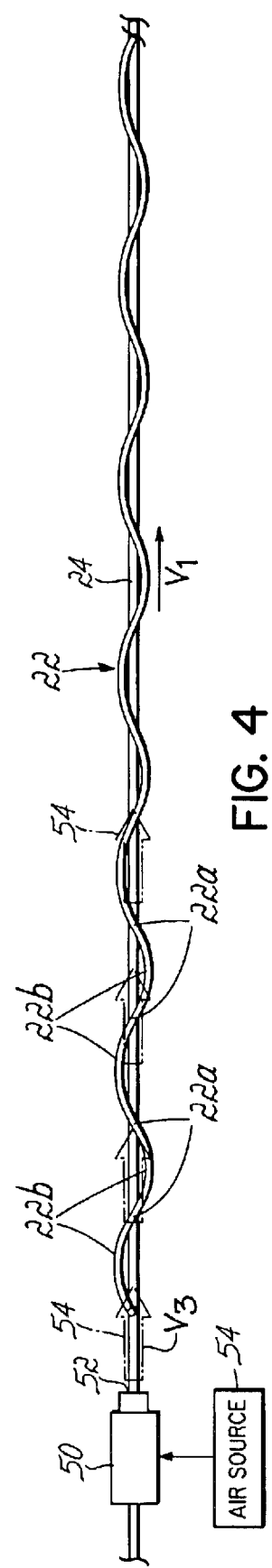
FIG. 3
FIG. 4

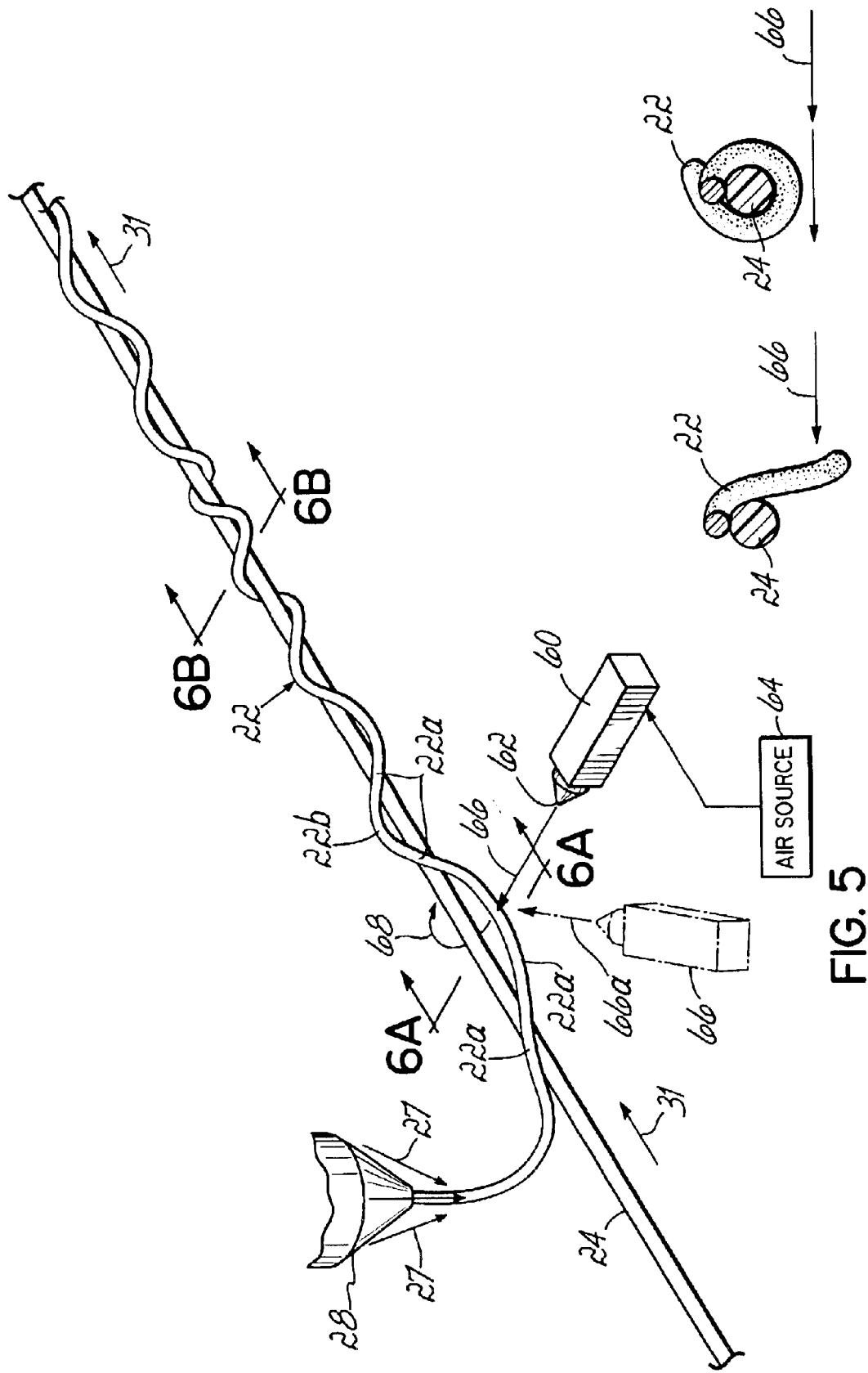

APPARATUS AND METHODS FOR APPLYING ADHESIVE FILAMENTS ONTO ONE OR MORE MOVING NARROW SUBSTRATES

FIELD OF THE INVENTION

The present invention generally relates to apparatus and methods for liquid material dispensing and, more specifically, to an apparatus and methods for dispensing controlled patterns of liquid adhesive filaments onto moving narrow substrates.

BACKGROUND OF THE INVENTION

Liquid adhesives, such as temperature and/or pressure sensitive adhesives, are frequently dispensed as a continuous adhesive filament with a controlled pattern onto a narrow substrate or a narrow width of a larger substrate. Conventional patterns have been created by impacting the adhesive filament with a plurality of air jets as the filament exits the discharge outlet of the dispenser or applicator. In the hot melt adhesive dispensing industry, one dispensing technique of this type is generally known as controlled fiberization or CF™, and is described, for example, in U.S. Pat. No. 4,785,996. The air jets impart a swirling effect to the adhesive filament that produces a generally back-and-forth pattern, which may have a regular or irregular appearance. Other conventional adhesive filament dispensing techniques and apparatus have been used for producing back-and-forth patterns of adhesive on a substrate, such as the vacillating pattern disclosed in U.S. Pat. No. 6,077,375 and the omega-shaped pattern disclosed in U.S. Pat. Nos. 6,461,430, 6,200,635 and 6,197,406.

Controlled fiberization and like filament dispensing techniques are used in the manufacture of hygienic articles, such as diapers, incontinence pads and other absorbent undergarments. In particular, controlled fiberization is a popular manufacturing technique employed for elasticizing specific areas of hygienic articles, such as the waistbands, leg cuffs, and standing leg gathers of diapers and adult incontinence products. To that end, continuous adhesive filaments are dispensed onto one or more individual moving elastic strands, either before or after the strand has contacted a substrate, for bonding each strand to the substrate. The adhesive filament drapes lengthwise along the moving strand about its circumference and secures the strand to the substrate after contact. In this manner, overlapping portions of the same material may be bonded together with each stretched elastic strand secured therebetween or two distinctly different substrates may be bonded together as a laminate with the stretched elastic strand secured therebetween.

With reference to FIG. 1, a conventional method of dispensing an adhesive filament 12 onto a moving strand 14 is illustrated. The strand 14 moves in a machine direction 19 at speeds of up to 1200 feet per minute past an adhesive applicator 16. The adhesive filament 12 is dispensed by the adhesive applicator 16 onto the strand 14 in a generally back-and-forth pattern relative to the direction of motion of strand 14 in the machine direction 19. The back-and-forth pattern is produced by multiple air jets 17 that steer the adhesive filament 12 transversely relative to the travel direction of strand 14. The transverse movement of the filament causes certain points or sections 12a of the filament 12 to contact the top of the strand 14 and other filament sections 12b to be airborne. The air jets 17 impart angular momentum to the airborne sections 12b that cause them to wrap about the circumference of the strand 14 downstream of the adhesive dispenser 16 until at least most of the adhesive filament 12 contacts the strand 14. The strand 14 is contacted with a substrate 18 and will be adhesively bonded to the substrate 18 by the adhesive filament 12. The strand 14, if elastic, may be stretched so that, upon attachment to the substrate 18, the substrate will be elasticized generally along a line defined by strand 14.

A significant problem is routinely encountered in the dispensing of such adhesive filaments 12 onto a moving strand 14. Specifically, the rapid movement of the strand 14 in the surrounding static or stagnant air induces air resistance or aerodynamic drag on the airborne sections 12b of filament 12. The direction of the force applied by the drag on the airborne filament sections 12b is opposite to the machine direction 19. As a result, the airborne filament sections 12b have a velocity that is different than the velocity of the strand 14 in the machine direction 19. The effects of drag persist until such time that the airborne filament sections 12b are wrapped about and adhesively bonded to strand 14. The drag causes the airborne filament sections 12b to stretch and lengthen relative to the contacting sections 12a. The lengthening induced by drag increases with increasing linear velocity of strand 14 in the machine direction 19. The pattern of the adhesive filament 12 on the strand 14 becomes significantly irregular so that lengths of the strand 14 may not be adequately coated and other portions may be heavily coated. As a result, the adhesive-coated strand 14 is not uniformly bonded along its length after it is applied to substrate 18. This adversely affects the properties of the bonded elastic strand 14 and substrate 18, such as product flexibility and softness.

Another problem occurs in those applications in which multiple closely-spaced moving strands are each receiving a discrete adhesive filament. Specifically, stretching or lengthening due to the drag forces can cause an adhesive filament intended to be received on one moving strand to contact and be received instead on an adjacent moving strand. A similar problem occurs in applications in which a single filament is being intentionally applied to multiple strands as certain strands may receive adhesive or a relatively heavy coat of adhesive while other strands are uncoated or irregularly coated. Either situation results in improper adhesive application and may result in a loss of usable product yield due to unadhered strands.

For these and other reasons, it would be desirable to provide an apparatus and method to compensate for the effects of the ambient environment on an adhesive filament being applied to a moving narrow substrate.

SUMMARY OF THE INVENTION

The invention provides an apparatus for manipulating an adhesive filament applied by a coating applicator in a back-and-forth pattern to a narrow substrate moving in an environment subject to aerodynamic drag or other disruptive aerodynamic forces or effects. The adhesive filament initially has airborne filament sections in a non-contacting relationship with the narrow substrate. According to the principles of the invention, the apparatus includes an air moving device mounted adjacent to a filament applicator. The air moving device includes at least one air discharge passage capable of directing a flow of air that impinges the adhesive filament discharged from the filament applicator. The flow of air acts on the airborne filament sections of the adhesive filament for improving the coating uniformity on the narrow substrate. For example, the air flow may cool the airborne sections and/or may transfer at least one of linear or angular momentum to the airborne filament sections.

According to the preferred embodiment, the flow of air is formed by one or more air jets that improve the uniformity of the application of the adhesive filament to the narrow substrate, which is moving with a significant linear velocity or speed in a machine direction. The air jets can, for example, compensate for forces acting on the airborne sections of the adhesive filament as the narrow substrate moves through the surrounding stagnant air. Moreover, in applications that dispense adhesive filaments onto individual moving narrow substrates, the air jets reduce stretching of the filaments so that a filament intended to be applied to one narrow substrate is less likely to contact and attach to an adjacent narrow substrate. In other applications that dispense an adhesive filament onto multiple moving narrow substrates, the air jets enhance the probability that the filament will uniformly contact and be distributed among the different substrates. The air jets improve the robustness of the adhesive filament by reducing thinning of the cross-sectional filament diameter. The air jets also afford an additional degree of control over the adhesive pattern previously unavailable with conventional adhesive filament dispensing techniques and apparatus.

According to the principles of the invention, a method is provided for dispensing an adhesive filament onto a narrow substrate moving in a machine direction. The method includes dispensing an adhesive filament toward the narrow substrate at an adhesive application location, moving the adhesive filament back-and-forth transverse to the machine direction, and applying the adhesive filament to the narrow substrate leaving airborne filament sections along the length of the narrow substrate downstream of the adhesive application location. The method further includes directing a flow of air at the airborne filament sections for improving the uniformity of the pattern. The air flow may be directed generally perpendicular relative to a plane containing the machine direction and the dispensed adhesive filament, before the adhesive filament contacts the strand, for transferring angular momentum to the airborne filament sections or may be directed generally parallel to the machine direction for transferring linear momentum to the airborne filament sections. Alternatively, the air flow may be directed at an acute angle relative to a plane containing the machine direction and the dispensed adhesive filament before the filament contacts the strand for transferring linear and angular momentum to the airborne filament sections. In certain embodiments, the temperature of the air may be less than a temperature of the adhesive filament so that the temperature of the airborne filament sections are quenched by the air flow.

These and other features, objects and advantages of the invention will become more readily apparent to those of ordinary skill in the art upon review of the following detailed description, taken in conjunction with the accompanying drawings.

BRIEF DESCRIPTION OF DRAWINGS

FIG. 3 is an enlarged top view of a portion of FIG. 2;

FIG. 4 is a perspective view similar to FIG. 2 according to an alternative embodiment of the invention;

FIG. 5 is a perspective view similar to FIGS. 2 and 4 according to an alternative embodiment of the invention;

FIG. 6A is a cross-sectional view taken generally along line 6A—6A in FIG. 5; and FIG. 6B is a cross-sectional view taken generally along line 6B—6B in FIG. 5.

DETAILED DESCRIPTION OF PREFERRED EMBODIMENTS

Although the invention will be described next in connection with certain embodiments, the invention is not limited to practice in any one specific type of adhesive dispensing system for applying an adhesive filament to a narrow substrate. It is contemplated that the invention can be used with a variety of adhesive systems that dispense adhesive filaments onto narrow substrates, including but not limited to adhesive dispensing systems configured to apply an adhesive filament to an elastic strand during the manufacture of hygienic articles. Exemplary adhesive dispensing systems in which the principles of the invention can be used are commercially available, for example, from Nordson Corporation (Westlake, Ohio) and such commercially available adhesive dispensing systems may be adapted for improving the effectiveness of the application process in accordance with the principles of the invention. The description of the invention is intended to cover all alternatives, modifications, and equivalent arrangements as may be included within the spirit and scope of the invention as defined by the appended claims. In particular, those skilled in the art will recognize that the components of the invention described herein could be arranged in multiple different ways.

Figure 2:
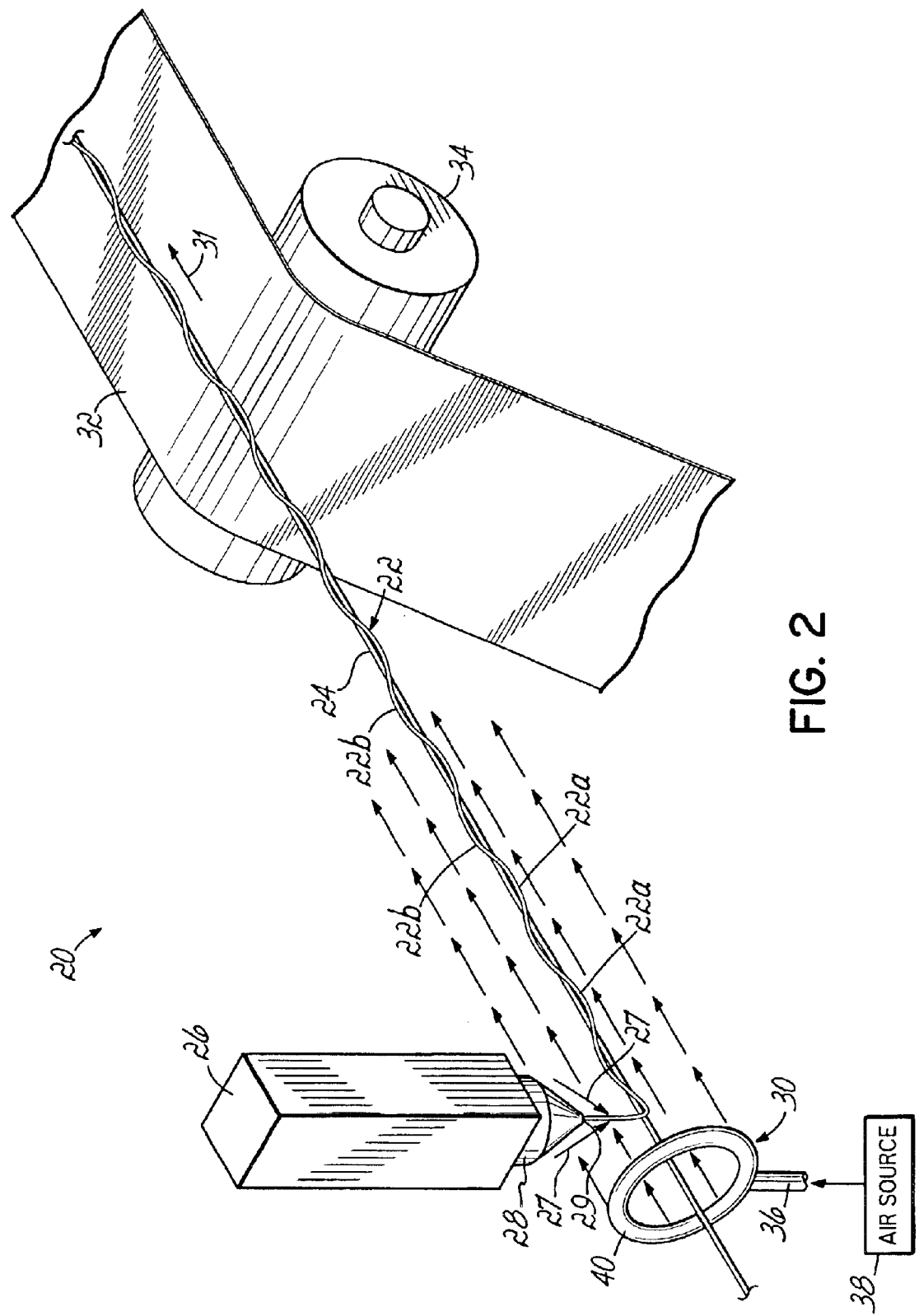
FIG. 2 is a perspective view of an adhesive filament being dispensed onto a strand according to the principles of the invention.

Referring to FIGS. 2 and 3, an exemplary coating application system, indicated generally by reference numeral 20, is provided which is capable of applying an adhesive filament 22 to a moving narrow substrate, such as strand 24, moved along a path by a parent machine fabricating a product, such as a hygienic article. The coating application system 20 generally includes a filament applicator 26 configured for dispensing adhesive filament 22 from a discharge outlet 29 of a nozzle 28, and an air moving device 30. Strand 24 is moved or transported in a travel path or machine direction, directed generally parallel to directional arrow 31, having a path segment proximate to and generally vertically beneath discharge outlet 29 of filament applicator 26. The speed or linear velocity, $V_1$, of strand 24 relative to the filament applicator 26 may be as fast as 1200 feet per minute. Typically, the strand 24 is formed from an elastic material, such as spandex or LYCRA®, although the invention is not so limited. The adhesive filament 22 dispensed from the discharge outlet 29 falls through an air gap separating nozzle 28 from strand 24 and periodically contacts and adheres to strand 24 along its length. The strand 24 is applied to a substrate 32, such as a woven or non-woven web, by the action of a nip roller 34 located downstream along machine direction 31 of the filament applicator 26 and is bonded by the adhesive filament 22 with substrate 32.

Filament applicator 26 generally comprises any device capable of applying an adhesive filament to a moving strand. Typically, the filament applicator 26 steers the adhesive filament 22 in a generally back-and-forth pattern imparted by, for example, air jets 27 impinging about the circumference of adhesive filament 22 immediately after discharge from nozzle 28. The generally back-and-forth pattern may be any pattern, either regular or irregular in nature, having airborne filament sections including but not limited to a swirl pattern, a vacillating or oscillating pattern, a generally sinusoidal pattern with repeating curvilinear segments, a curvilinear pattern that is irregular in period, or a sawtooth or zig-zag pattern with either a regular or irregular period. It is appreciated that the filament applicator 26 may discharge viscous material in a swirl pattern that ultimately defines discrete areas of adhesive in a pattern consisting of solid dots, that may or may not be interconnected by thinner intervening filament sections, arising from airborne sections, and which may be either irregular or regular in nature With continued reference to FIGS. 2 and 3, air moving device 30 comprises a conduit 36 extending to an air source 38 and a round, tubular head 40. Tubular head 40 incorporates a plurality of air discharge passages or apertures 42 (FIG. 3) each individually defining an air stream or impingement jet that collectively define an air flow, indicated schematically on FIG. 3 by directional arrows labeled with reference numeral 44. The tubular head 40 may be spiraled so that the strand 24 may be inserted or threaded into the air moving device 30 through the gap created by the spiral. Strand 24 is generally aligned lengthwise with the centerline of the tubular head 40. The apertures 42 are oriented relative to the strand 24 such that the impingement jet from each aperture 42 is directed generally parallel to machine direction 31. Certain of the apertures 42 may be oriented about the circumference of tubular head 40 so that the air flow therefrom has an acute inclination angle relative to machine direction 31, typically less than about 5°, indicated schematically on FIG. 3 by directional arrows in phantom labeled with reference numeral 44a. Such an inward orientation of apertures 42 provides a convergent air flow for constructively adding to or otherwise reinforcing the angular momentum imparted to the adhesive filament 22 by the filament applicator 26 and enhances the wrapping rate about strand 24. Typically, the apertures 42 are arranged about tubular head 40 such that adjacent pairs of apertures 42 have equal inter-aperture angular spacings, although the invention is not so limited.

As best shown in FIG. 3, the effect of the impingement jets from apertures 42 is to reduce irregularities in the generally back-and-forth pattern characterizing adhesive filament 22. The transverse movement of the adhesive filament 22 relative to strand 24 provided by filament applicator 26 causes certain points or sections 22a of filament 22 to contact the top of the strand 24 nearest to discharge outlet 29 and other filament sections 22b to be airborne with a non-contacting relationship with strand 24. The airborne filament sections 22b extend transversely on opposite sides of the strand 24. As the stand 24 moves in machine direction 31 toward the nip roller 34, the airborne filament sections 22b progressively wrap about or otherwise contact the strand 24 and, before strand 24 contacts substrate 32, the airborne filament sections 22b have contacted the strand 24 and are no longer airborne.

The flow of air streaming from apertures 42 has a velocity, $V_2$ selected to effectively compensate for the aerodynamic drag or other disruptive aerodynamic forces or effects acting on the airborne sections 22b of adhesive filament 22. Typically, the velocity, $V_2$, of the air streaming from the apertures 42 is approximately equal to the linear velocity, $V_1$, of the strand 24 along machine direction 31, although the invention is not so limited. In particular, parameters such as the cross-sectional areas of the apertures 42, the mass flow rate of the air to the apertures 42, and the air pressure supplied to tubular head 40 may be varied to project the respective impingement air jets with the required velocity. It is contemplated that the parameters characterizing each individual aperture 42 may be varied for systematically tailoring the individual velocities, including speed and direction, of each of the impingement jets.

Figure 1:
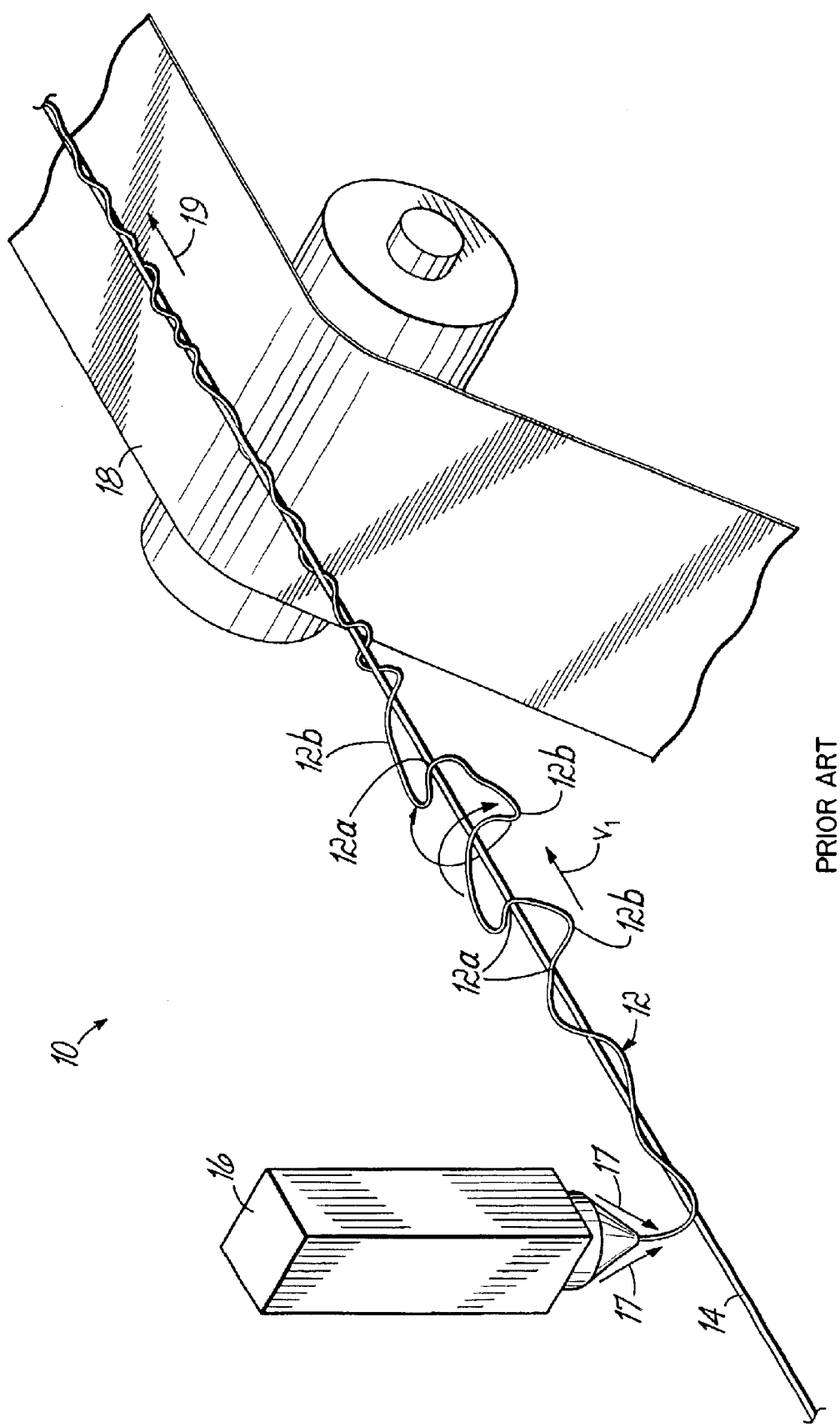
FIG. 1 is a perspective view of an adhesive filament being dispensed onto a narrow substrate according to the prior art.

The linear momentum imparted by the air flows from apertures 42 is directed generally parallel to the machine direction 31 for increasing the effective linear velocity or speed of the airborne filament sections 22b of adhesive filament 22 to compensate for aerodynamic drag or other disruptive aerodynamic forces or effects. As a result, the airborne sections 22b are less likely to stretch or elongate, which improves the application effectiveness and the uniformity of adhesive application to strand 24. The improvement is apparent from a comparison of the pattern of adhesive filament 22 coating strand 24 with the pattern of adhesive filament 12 coating filament 14 (FIG. 1). The air flow from apertures 42 may be symmetrical or asymmetrical, as required to provide the necessary compensation, about the axis line defined by strand 24 along the machine direction 31. For example, the centerline of tubular head 40 may coincide with the axis line of strand 24 or may be offset vertically so that its center and the axis line of strand 24 are not coaxial or coincident. Alternatively, the axis line of strand 24 may be inclined relative to the centerline of the tubular head 40.

The air flow from apertures 42 of air moving device 30 may be provided at a temperature that is less than the temperature of the adhesive filament 22 near the point at which filament 22 exits nozzle 28 of filament applicator 26. Typically, the temperature of the air provided from air moving device 30 is at or near ambient temperature, although the invention is not so limited. The reduced temperature of the air quenches the material forming the adhesive filament 22 and, in particular, the material forming the airborne sections 22b of adhesive filament 22. The effect of the reduction in temperature is to increase the filament viscosity, which in turn reduces the lengthening or stretching of the airborne sections 22b of adhesive filament 22 due to movement through the ambient air environment along machine direction 31.

Collectively, the impingement jets from apertures 42 effectively compensate for aerodynamic drag or other disruptive aerodynamic forces or effects due to the surrounding air by adding linear momentum to the airborne sections 22b so that the generally back-and-forth pattern traced by the adhesive filament 22 on the strand 24 is more uniform and has a better defined periodicity or frequency. In addition, the impingement jets from apertures 42 may add angular momentum that speeds the angular velocity of the airborne sections 22b of adhesive filament 22 about strand 24 so that wrapping or winding is accelerated. As a result, the airborne sections 22b of adhesive filament 22 are less likely to contact nearby objects, such as an adjacent strand also receiving another adhesive filament (not shown).

The impingement jets provided by the streams of air exiting apertures 42 are independent of the air jets 27 relied upon by the filament applicator 26 for imparting the generally back-and-forth pattern to the adhesive filament 22. Typically, the streams of air from air jets 27 are dispensed in a common plane with the adhesive filament 22 at its point of emission from the discharge outlet 29 of nozzle 28.

In use and with reference to FIGS. 2 and 3, strand 24 is moved in machine direction 31 including a path segment proximate to the discharge outlet 29 in nozzle 28 of filament applicator 26. The adhesive filament 22 dispensed from the filament applicator 26 is guided by air jets 27 in a generally back-and-forth pattern relative to the machine direction 31. Sections 22a of the adhesive filament 22 contact strand 24 immediately after dispensing and airborne sections 22b of the adhesive filament 22 have a non-contacting relationship with strand 24. The impingement jets provided by the streams of air exiting apertures 42 of air moving device 30 act on the airborne sections 22b by adding linear momentum so that the airborne sections 22b are less likely to lengthen. The streams of air exiting apertures 42 may also add angular momentum to the airborne sections 22b for increasing their wrapping rate about the strand 24. In addition, the air streaming from the apertures 42 cools the airborne sections 22b, which increases the viscosity so as to counteract the lengthening produced by aerodynamic drag or other disruptive aerodynamic forces or effects. The nip roller 34 presses the strand 24 onto substrate 32 and the adhesive filament 22 adhesively bonds the strand 24 with the substrate 32.

With reference to FIG. 4 in which like reference numerals refer to like features in FIGS. 2 and 3, coating application system 20 is provided with an air moving device 50 positioned upstream of the filament applicator 26 and spaced transversely from the strand 24. Air moving device 50 is configured for emitting a flow or stream of air, indicated schematically on FIG. 4 by a directional arrow labeled with reference numeral 54, directed generally parallel to machine direction 31 and, to that end, incorporates one or more air discharge passages or apertures 52. Each aperture 52 operates as an impingement jet by projecting a flow or stream of air originating from air supplied by air source 54. The impingement jets defined by apertures 52 compensate for aerodynamic drag or other disruptive aerodynamic forces or effects acting on the airborne sections 22b of adhesive filament 22 that arise from motion in the ambient air surrounding strand 24. The velocity, $V_3$, of the air stream is selected accordingly and, in certain embodiments, may be approximately equal to the speed of strand 24 in the machine direction, as described herein with regard to air moving device 30.

With reference to FIG. 5 in which like reference numerals refer to like features in FIGS. 2–4, coating application system 20 is provided with an air moving device 60 that directs a flow or stream of air, indicated schematically on FIG. 5 by a directional arrow labeled with reference numeral 66, from at least one air discharge passage or aperture 62 toward the adhesive filament 22 and strand 24. Air is supplied to the air moving device 60 from an air source 64. Each aperture 62 is oriented relative to strand 24 so that the impingement jet or air flow is directed generally perpendicular to the machine direction 31, as indicated by direction arrow 66. In addition, air flow 66 is oriented generally perpendicular to a plane containing the strand 24 and the adhesive filament 22 when it in the air gap between discharge outlet 29 and the strand 24. Air flow 66 is generally directed below or beneath strand 24, as best shown in FIG. 6A, so that the air stream emitted from aperture 62 constructively adds to or otherwise reinforces the angular momentum imparted to the airborne sections 22b of adhesive filament 22 by the filament applicator 26, which increases the wrapping rate of adhesive filament 22 about strand 24.

In particular and with reference to FIG. 6A, the airborne sections 22b are spaced from the strand 24 immediately before the strand 24 moves to a position along machine direction 31 in which the air flow from discharge aperture 62 strikes the adhesive filament 22. The air flow from discharge aperture 62 transfers additional angular momentum to the airborne sections 22b, which accelerates the airborne sections 22b to increase their angular velocity and the effective wrapping rate of airborne sections 22b about strand 24. As a result, the adhesive filament 22 wraps more uniformly about the strand 24. In addition, the temperature of the air exiting air moving device 60 may be less than the temperature of the adhesive filament 22 so that material forming the airborne sections 22b is quenched. Shortly downstream, the adhesive filament 22 is wrapped about the strand 24 with a substantially contacting relationship, as indicated in FIG. 6B.

It is contemplated by the invention that each discharge aperture 62 may be arranged to direct its air flow at an acute angle relative to the machine direction 31, as shown by the air flow indicated schematically on FIG. 5 by a directional arrow labeled with reference numeral 66a. Air flow 66a is also oriented with an acute angle relative to a plane containing the strand 24 and the adhesive filament 22 in the air gap between discharge outlet 29 and the strand 24. In this manner, the impingement jet provided by each aperture 62 may provide linear momentum to the airborne sections 22b in the machine direction 31 for reducing lengthening, as well as angular momentum for increasing the wrapping rate of the airborne sections 22b about the strand 24. The invention also contemplates that a plurality of air moving devices 60 may be employed for reducing the effects of aerodynamic drag or other disruptive aerodynamic forces or effects in accordance with the principles of the invention.

A number of factors contribute to the improved results of the invention. Generally, these relate to the movement of airborne sections of the adhesive filament through the ambient air after other sections of the adhesive filament contact the strand or stands. The air moving devices of the invention reduce the width or amplitude of the pattern transverse to the machine direction for maintaining control of the filament location on the strand. That is, the filament pattern should not be so wide as to hang or drape considerably off the strand. According to the principles of the invention, the air moving device may increase or boost the linear momentum of the airborne filament sections in the machine direction for increasing the speed of the airborne filament sections to more closely match the speed of the strand in the machine direction. In the alternative or in addition, the air moving device may increase the angular momentum of the airborne filament sections by applying a force that is non-parallel to the machine direction for increasing the wrapping rate of the airborne filament sections about the strand. Moreover, the air flow from the air moving device may cool the airborne filament sections for increasing their viscosity and make the airborne filament sections less susceptible to stretching. As a result, the strand receives a more uniform coating of adhesive rather than a coating having spaced-apart distinct adhesive masses.

While the present invention has been illustrated by a description of various preferred embodiments and while these embodiments have been described in some detail, it is not the intention of the Applicants to restrict or in any way limit the scope of the appended claims to such detail. Additional advantages and modifications will readily appear to those skilled in the art. The various features of the invention may be used alone or in numerous combinations depending on the needs and preferences of the user. This has been a description of the present invention, along with the preferred methods of practicing the present invention as currently known. However, the invention itself should only be defined by the appended claims, wherein

What is claimed is:

1. An apparatus for applying an adhesive filament in a back-and-forth pattern onto at least one narrow substrate moving in a machine direction, comprising:

an applicator capable of dispensing the adhesive filament onto the at least one narrow substrate and capable of impinging the adhesive filament with a plurality of air jets to create the back-and-forth pattern with airborne filament sections extending from the at least one narrow substrate transverse to the machine direction; and an air moving device mounted adjacent to said applicator, said air moving device including at least one air discharge passage capable of directing a flow of air that impinges the airborne filament sections downstream in the machine direction from said applicator in order to improve the uniformity of the pattern.

2. The apparatus of claim 1, wherein said at least one air discharge passage is oriented such that said flow of air is approximately perpendicular to a plane containing the machine direction and the adhesive filament before the adhesive filament contacts the at least one narrow substrate.

3. The apparatus of claim 1, wherein said at least one air discharge passage is oriented such that said flow of air is aligned at an acute angle relative to a plane containing the machine direction and the adhesive filament before the adhesive filament contacts the at least one narrow substrate.

4. The apparatus of claim 1, wherein said air moving device further includes a plurality of air discharge passages arranged to be capable of directing a corresponding plurality of air flows about a circumference of the at least one narrow substrate.

5. The apparatus of claim 4, wherein said air moving device comprises an annular tube having said discharge passages, said annular tube positioned relative to said applicator such that the at least one narrow substrate moves in the machine direction circumferentially inside said annular tube.

6. The apparatus of claim 1, wherein said air jets are oriented in a first direction for impinging the adhesive filament to create the back-and-forth pattern, and said at least one air discharge passage of said air moving device directs said flow of air in a second direction that differs from said first direction.

7. A method for dispensing an adhesive filament onto at least one narrow substrate moving in a machine direction, comprising:

dispensing an adhesive filament toward the at least one narrow substrate at an adhesive application location;

impinging the adhesive filament with a plurality of air jets to move the adhesive filament with a back-and-forth pattern transverse to the machine direction;

applying the adhesive filament to the at least one narrow substrate leaving airborne filament sections extending transversely of the at least one narrow substrate along the length of the at least one narrow substrate downstream of the adhesive application location; and directing a flow of air at the airborne filament sections that impinges the transversely-extending airborne filament sections downstream in the machine direction from the adhesive application location.

8. The method of claim 7, wherein a temperature of the air is less than a temperature of the adhesive filament, and the directing of the flow of air further comprises:

quenching the temperature of the airborne filament sections with the flow of air.

9. The method of claim 7, wherein the flow of air is directed generally perpendicular relative to a plane containing the machine direction and the dispensed adhesive filament, and the directing of the flow of air further comprises:

transferring angular momentum to the airborne filament sections.

10. The method of claim 7, wherein the flow of air is directed at an acute angle relative to a plane generally containing the machine direction and the dispensed adhesive filament, and the directing of the flow of air further comprises:

transferring angular momentum to the airborne filament sections; and transferring linear momentum to airborne filament sections.

11. An apparatus for applying an adhesive filament onto at least one narrow substrate moving in a machine direction, comprising:

an applicator configured to dispense the adhesive filament onto the narrow substrate in a back-and-forth pattern having airborne filament sections extending transversely relative to the machine direction; and an air moving device mounted adjacent to said applicator, said air moving device including at least one air discharge passage capable of directing a flow of air toward the airborne filament sections downstream from said applicator in order to improve the uniformity of the pattern, and said at least one air discharge passage oriented relative to the at least one narrow substrate such that said flow of air is approximately parallel to the machine direction.

12. A method for dispensing an adhesive filament onto at least one narrow substrate moving in a machine direction, comprising:

dispensing an adhesive filament toward the at least one narrow substrate at an adhesive application location, moving the adhesive filament back-and-forth transverse to the machine direction;

applying the adhesive filament to the at least one narrow substrate leaving airborne filament sections along the length of the narrow substrate downstream of the adhesive application location; and directing a flow of air at the airborne filament sections and generally parallel to the machine direction to transfer linear momentum to the airborne filament sections and thereby improve pattern uniformity.

* * * * *